(12) United States Patent
De Buck

(10) Patent No.: US 9,622,838 B2
(45) Date of Patent: Apr. 18, 2017

(54) PRECISION ATTACHMENT SYSTEM WITH INDIRECT RETAINER

(71) Applicant: Vincent De Buck, Sint-Pauwels (BE)

(72) Inventor: Vincent De Buck, Sint-Pauwels (BE)

( * ) Notice: Subject to any disclaimer, the term of this patent is extended or adjusted under 35 U.S.C. 154(b) by 226 days.

(21) Appl. No.: 14/468,124

(22) Filed: Aug. 25, 2014

(65) Prior Publication Data

US 2015/0072310 A1 Mar. 12, 2015

(30) Foreign Application Priority Data

Sep. 10, 2013 (BE) .................................... 2013/0589

(51) Int. Cl.
| | |
|---|---|
| *A61C 13/225* | (2006.01) |
| *A61C 13/265* | (2006.01) |
| *A61C 8/00* | (2006.01) |
| *A61C 13/275* | (2006.01) |
| *A61C 5/70* | (2017.01) |

(52) U.S. Cl.
CPC ............ *A61C 13/2656* (2013.01); *A61C 5/70* (2017.02); *A61C 8/00* (2013.01); *A61C 8/0048* (2013.01); *A61C 13/2255* (2013.01); *A61C 13/275* (2013.01)

(58) Field of Classification Search
CPC ......... A61C 13/2656; A61C 5/08; A61C 8/00; A61C 8/0048; A61C 12/2255; A61C 12/275
See application file for complete search history.

(56) References Cited

U.S. PATENT DOCUMENTS 4,204,321 A * 5/1980 Scott .................. A61C 13/2656
433/177
5,678,997 A * 10/1997 De Buck ............ A61C 13/2656
433/177

FOREIGN PATENT DOCUMENTS

| | | |
|---|---|---|
| CH | 597843 A5 | 4/1978 |
| DE | 3839112 A1 | 6/1989 |
| DE | 4422773 A1 | 1/1996 |
| EP | 0473933 A1 | 3/1992 |
| FR | 2566263 A1 | 12/1978 |

* cited by examiner

*Primary Examiner* — Christopher D Prone
(74) *Attorney, Agent, or Firm* — Chen-Chi Lin

(57) ABSTRACT

A precision attachment system for mounting a dental prosthesis to a retention bar having a round section and an off-centered support section, and a C-shaped retention clip which is incorporated into the dental prosthesis and encloses the round section. A spacer clip is adapted for both the retention clip and the retention bar. The contact of the dental prosthesis with the indirect retainer surface of the support section prevents the free-end saddles from lifting off the alveolar ridge. The resilience of the dental prosthesis in the direction of the atrophying alveolar ridge remains possible. The indirect retainer surface and the slotted flange of the housing guide the retention clip to the round section when assembled with the retention bar.

4 Claims, 4 Drawing Sheets

PRECISION ATTACHMENT SYSTEM WITH INDIRECT RETAINER

CROSS-REFERENCE TO RELATED APPLICATIONS

This application claims priority to Belgian patent application No. BE 2013/0589, filed Sep. 10, 2013, entitled "SYSTÈME D'ATTACHEMENT DE PRÉCISION AVEC RÉTENTION INDIRECTE", filed by the same inventor and is incorporated in its entirety herein by reference.

BACKGROUND OF THE INVENTION

1. Field of the Invention

This invention relates to a device to retain a dental prosthesis in the mouth, commonly known as a precision attachment. More particularly this invention concerns a system for securing a patient-detachable dental prosthesis to a retention bar which is mounted in the mouth, typically with the ends of the retention bar secured in implanted abutments or in crowns on teeth with the retention bar extending along and above the gum line where teeth are missing. A matching C-shaped component is included in the dental prosthesis which connects with the retention bar by means of a snap mechanism.

2. Discussion of Related Art

The retention clip and retention bar as described in the patent of Helmut Hader CH597843 are commercially available as PRECI-HORIX, see Brochure BRO-273.E-ed.B of Alphadent NV, Waregem, Belgium. This attachment system consists of a flexible C-shaped retention clip and a retention bar with a round section and a support section, an auxiliary spacer clip, special retention clips with reduced or stronger retention, a paralleling instrument for the retention bar, an insertion tool and a metal housing. These extra components facilitate the incorporation and the servicing of the precision attachment.

The paralleling instrument aligns the parallel walled support section of the retention bar to the path of insertion of the prosthesis.

The C-shaped retention clip has two flexible retention wings engaging the lateral sides of the round section of the retention bar. The retention clip is flexible and snaps by means of an insertion instrument behind retention ledges which have been provided in the dental prosthesis. The retention clip can easily be removed and replaced by a new retention clip with equal, less or more retention. The new retention clip is pressed in exactly the same place.

The ease of replacement of the retention clip is obtained by the use of a spacer clip during the processing of the dental prosthesis and which does not adhere to the acrylic resin of the dental prosthesis. After processing the acrylic resin of the dental prosthesis, the spacer clip is removed and will have created a void with a retention ledge which will retain the retention clip in place during function. The spacer clip also creates a passage for easier replacement of the retention clip. This passage is obtained by both extended spacer wings of the spacer clip which align along the support section of the retention bar.

Another property of the spacer clip is to align multiple retention clips parallel to the path of insertion of the dental prosthesis. As the extended spacer wings of the spacer clip all maintain close contact with the support section of the retention bar, parallelism and a neutral position are guaranteed for all retention clips.

In order to guarantee a perfect fit of the retention clip in the dental prosthesis, a metal housing is provided which has the exact inner shape of the retention clip and provides a retention ledge in metal rather than in the acrylic of the dental prosthesis which is easily damaged after a few replacements.

The dental prosthesis must be as stable as possible during its functional use. This presents special problems but is necessary to ensure comfort and functionality for the patient. In particular, when only two abutments are in the jaw which are connected with a retention bar, and the free-end saddles of the dental prosthesis also require support from the alveolar ridge, it is difficult to obtain a balance of stability and flexibility.

The mucosa which provides support to the free-end saddles can be slightly compressed and the alveolar ridge is bound to atrophy in time. This implies that the dental prosthesis must allow for a hinging movement in the direction of the compressed tissue or atrophied ridge. If the connection of the dental prosthesis to the retention bar is too rigid, the precision attachments and the abutments with supporting bone structure can be damaged.

The precision attachment described in the patent of Helmut Hader CH5957843 will allow for this movement. The dental prosthesis is able to rotate around the axis of the round section of the retention bar and allows the free-end saddles to compress the mucosa without putting torque on the retention bar and its abutments. This movement is commonly called resilience. The free-end saddles of the prosthesis, however, can also rotate in the opposite direction and lift off from the soft tissue when the patient is chewing sticky food or pressing with the tongue against the front teeth. This is particularly troublesome and causes discomfort and embarrassment to the patient.

Another frequent problem encountered with the above precision attachment is that the round section does not align with the retention wings of the retention clip when the patient places the dental prosthesis in his mouth. This causes the retention wings to be bent inwards and destroy the retention clip.

The patent application by Niklaus Gerhard DE3839112 describes a solution for a retention bar and a metal retention clip to allow rotation of the dental prosthesis in only one direction. The retention bar is asymmetrical in cross section being on one side U-shaped and on the other side ovoid shaped. This system has some drawbacks as it is not based on the use of a spacer clip which provides the advantages of ease of processing of the dental prosthesis and ease of replacement of the retention clips. The metal retention clip obtains snap retention at the ovoid side of the bar only, necessitating a long and flexible retention wing engaging the ovoid shape. A further drawback is that there is no provision to process the metal retention clip in a neutral position being in contact with the U-shaped surface. This is of considerable concern when the metal retention clip needs to be replaced in the patient's mouth with autopolymerizing resin.

The patent application by Milosevic Bozidar EP0170555 describes a metal retention clip which engages unilaterally with the undercut of an asymmetrical retention bar and simultaneously engages with parallel walled segments of the retention bar. This type of attachment does not have an indirect retainer in combination with a resilient dental prosthesis as this invention does.

OBJECTS OF THE INVENTION

Therefore what is needed is an improved retention bar system than the one described in the aforementioned patent of Helmut Hader CH5957843. This improved retention bar system should prevent the free-end saddles of the dental prosthesis from separating from the mucosa. These problems are overcome by the use of an indirect retainer in combination with a direct retainer: the direct retainer is the C-shaped retention clip and the round section of the retention bar which retains and prevents dislodgement. The indirect retainer is the component that assists the direct retainer in preventing displacement of the free-end saddle away from the mucosa. This is obtained through a lever action on the side opposite the fulcrum line which is located in the centre of the round section.

The improved retention bar system should thus have a C-shaped retention clip engaging the round bar section, functioning as a direct retainer and a support section with an indirect retainer surface making contact with the dental prosthesis. The support section at the side of the free-end saddles should not make contact with the dental prosthesis when the free-end saddles move in the direction of the compressed mucosa or atrophied alveolar ridge. The ease of replacement of the retention clip via a passage in the dental prosthesis, the guaranteed parallelism of the retention clips and the neutral position of the retention clips during processing should be maintained by means of an adapted spacer clip.

The support section should guide the round section of the retention bar to the centre of the retention clip to avoid damage to the retention clip during placement of the dental prosthesis. This guidance can be further optimized by the use of a housing of which at least one extremity is closed with a slotted flange guiding the round section of the retention bar towards the centre of the retention clip when the patient places the dental prosthesis in the mouth.

SUMMARY OF THE INVENTION

The invention is set forth and characterized in the main claim, while the dependent claims describe the other characteristics of the invention.

According to the invention, an attachment system is provided for mounting a dental prosthesis to an edentulous alveolar ridge area which comprises: a retention bar which is secured to abutments, a C-shaped flexible retention clip which is incorporated into the removable dental prosthesis and encloses by means of two retention wings a round section of the retention bar by means of two retention wings, commonly referred to as direct retention.

The round section of the retention bar creates a fulcrum line of the free-end saddles of the dental prosthesis. This rotation is in the direction of the mucosa under occlusal load when the mucosa is compressed or when the alveolar ridge atrophies.

The retention bar also has a support section between the round section and the underlying mucosa. This support section is off-centred and has at one side sufficient width to provide a passage for the replacement of the retention clip and to make contact between the dental prosthesis and an indirect retainer surface. The indirect retainer surface prevents movement of the free-end saddles of the dental prosthesis away from its tissue support by means of lever action.

The attachment system is supplied with a spacer clip with two spacer wings of which one spacer wing is extended along the support section opposite the indirect retainer surface. The spacer clip provides ease of processing and guarantees a neutral position and parallelism when multiple retention clips are used. Moreover, it provides a passage for the replacement of the retention clips. The resilience of the free-end saddles in the direction of the compressed mucosa or atrophied bone is not interfered with as the zone underneath the round section of the retention bar opposite the indirect retainer surface is void and will not make contact with the dental prosthesis.

The metal housing with a slotted flange and the indirect retainer surface guide the centre of the retention clip towards the centre of the round section when the dental prosthesis is placed in the mouth by the patient.

BRIEF DESCRIPTION OF THE DRAWING

The characteristics of the invention will be clear from the following description of a preferential form of embodiment, given as a non-restrictive example.

Figure 1:
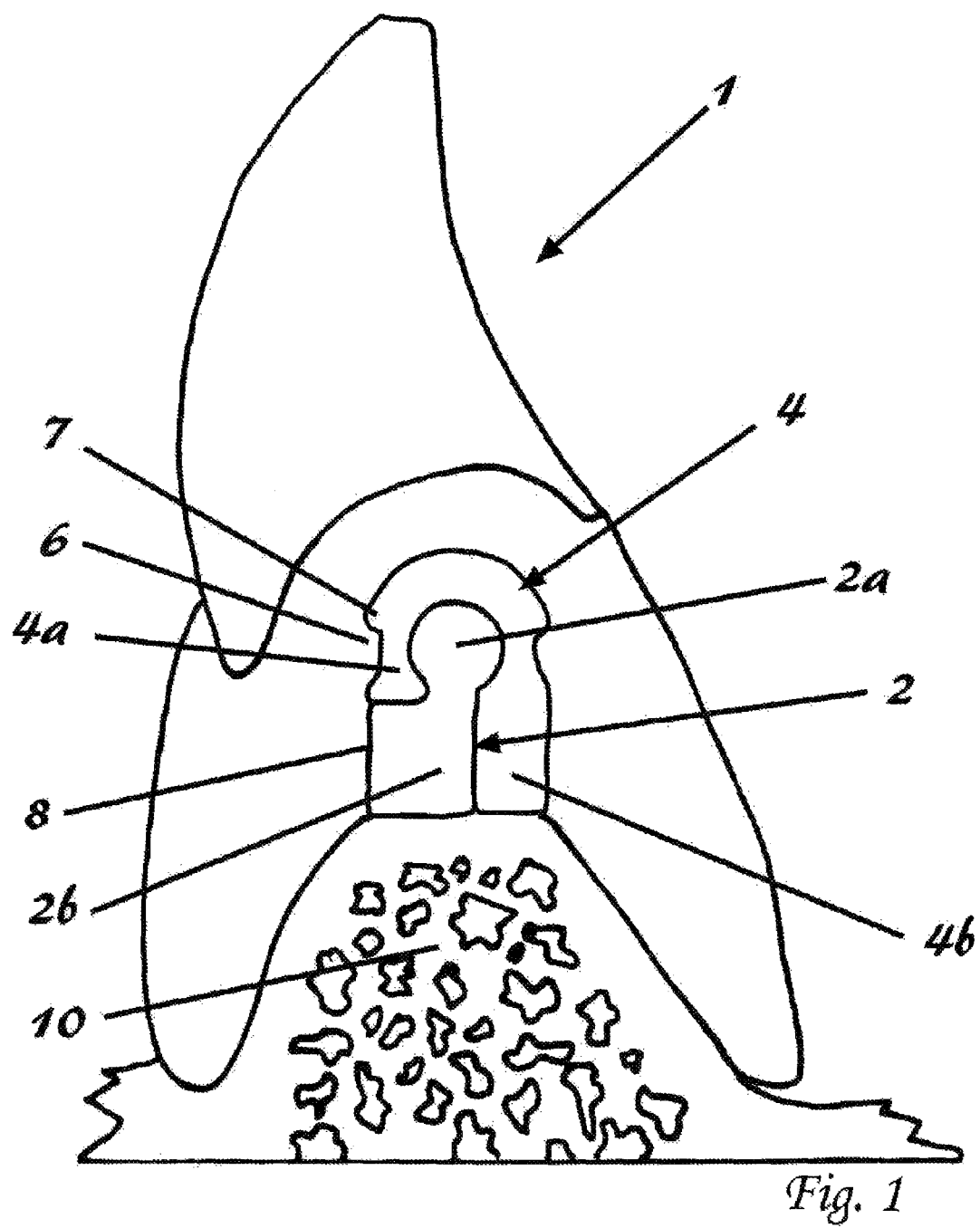
FIG. 1 is a vertical cross section through a dental prosthesis and a retention bar with the spacer clip incorporated.
Figure 2:
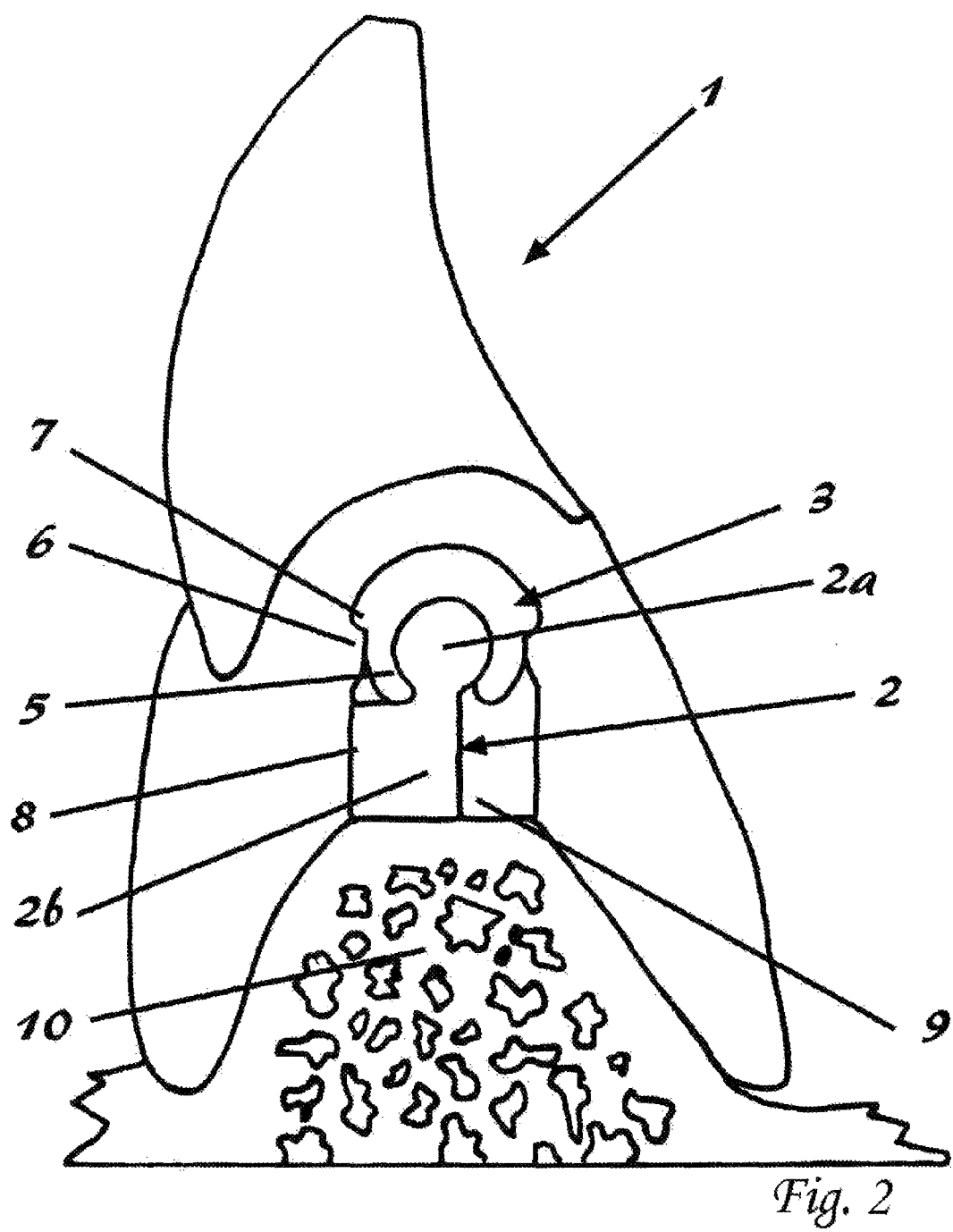
FIG. 2 is a vertical cross section through a dental prosthesis with the retention clip of this invention incorporated.
Figure 3:
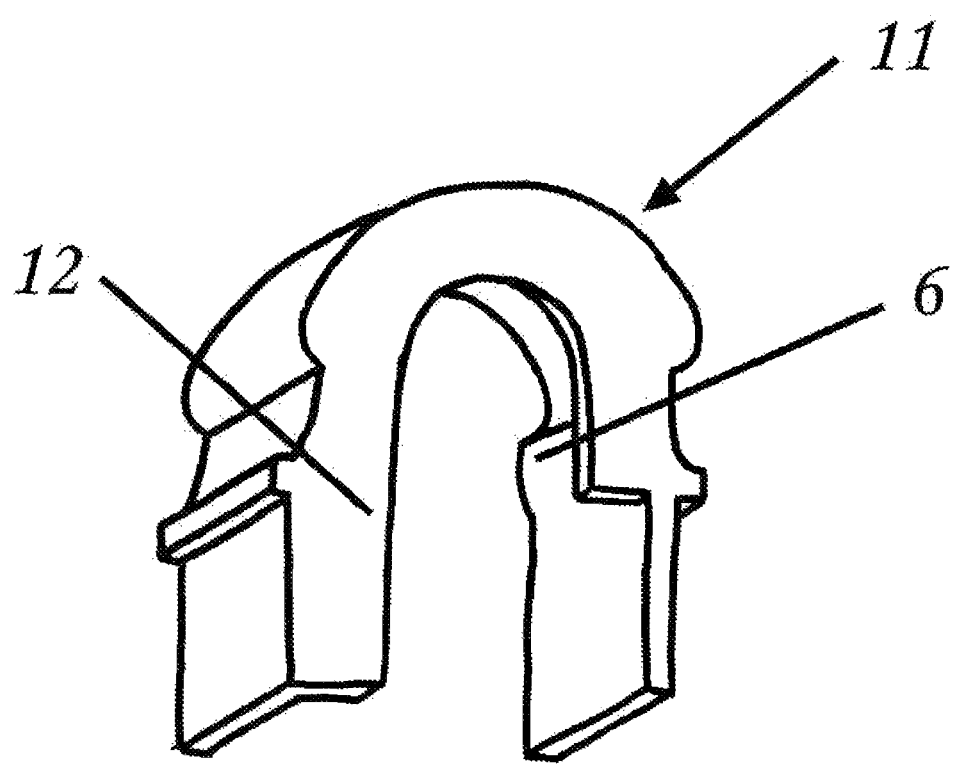
FIG. 3 is a housing with a slotted flange.
Figure 4:
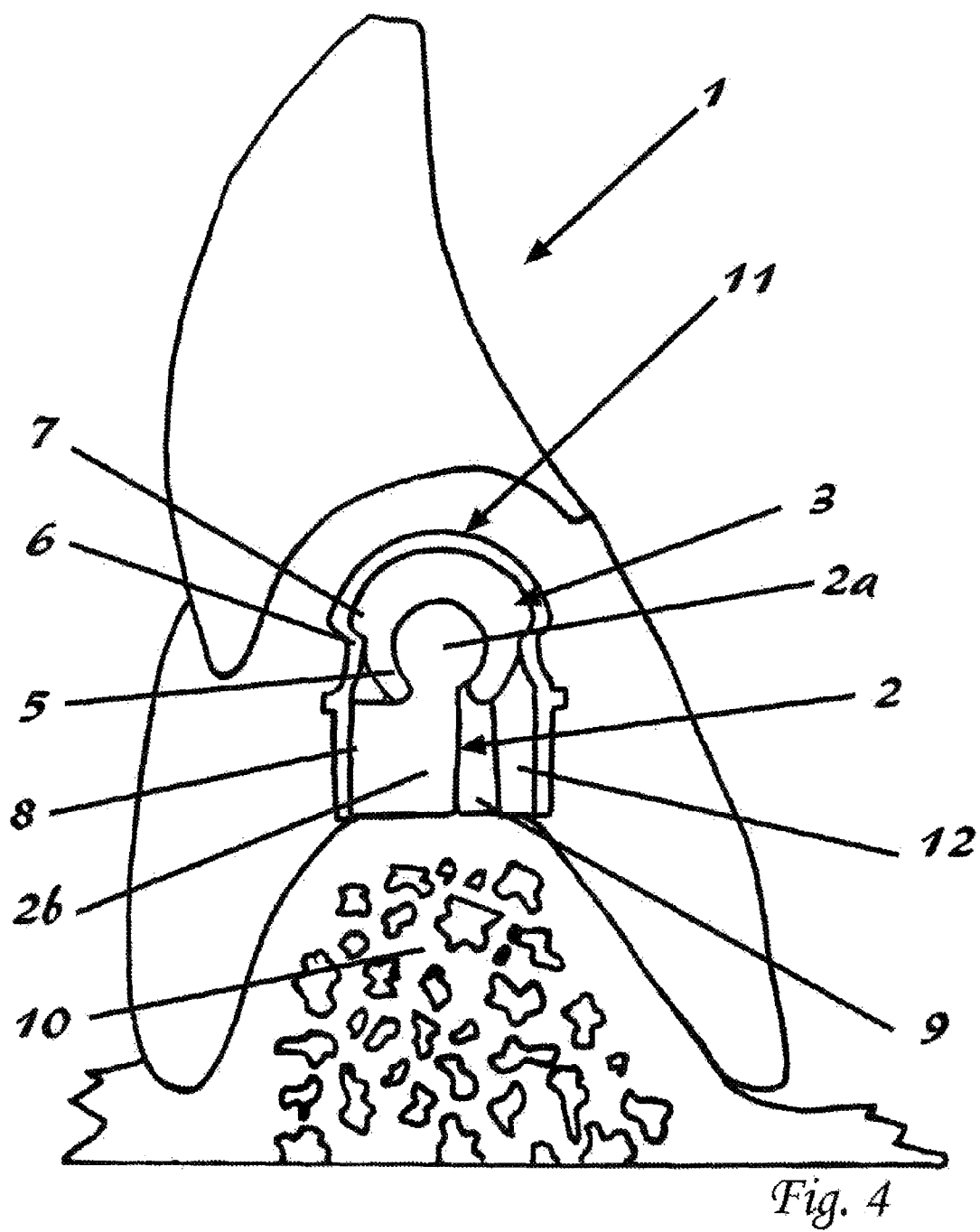
FIG. 4 is a vertical cross section through a dental prosthesis with a metal housing with slotted flange and a retention clip.

The numbers correspond with the following descriptions:
1 dental prosthesis
2 retention bar
2a round section
2b support section
3 retention clip
4 spacer clip
4a spacer wing
4b extended spacer wing
5 retention wing
6 retention ledge
7 shoulder
8 indirect retainer surface
9 passage
10 alveolar ridge
11 housing
12 slotted flange

DETAILED DESCRIPTION

The retention clip (3) in an elastic material in its preferred embodiment is an open tubular segment having a C-shaped transverse cross section with retention wings (5). The outer aspects of the retention clip (3) have shoulders (7) to engage with the retention ledges (6) in the removable dental prosthesis (1).

The retention bar (2) in its preferred embodiment has a round section (2a) which has dimensions to couple with the retention clip (3). The round section (2a) is supported by an off-centred support section (2b). The support section (2b) is on one side sufficiently wide to create a passage (9) for the retention clip (3). The opposing side is less wide and requires an asymmetrical spacer clip (4) which has only one extended spacer wing (4b) to guarantee a passage (9) for the retention clip (3).

The spacer clip (4) in its preferred embodiment is a tubular plastic segment that has an identical C-shaped transverse dorsal cross section as the retention clip (3). The spacer clip (4) includes spacer wings (4a) which become gradually wider in order to provide extra space in the dental prosthesis (1) so that the retention clips (5) can open flexibly to engage or disengage the round section (2a) of the retention bar (2).

The outer portions of the side walls of the spacer clip (4) have shoulders (7) to create retention ledges (6) for the retention clip (3) in the removable dental prosthesis (1) during processing.

One extended spacer wing (4b) extends along the support section (2b) of the retention bar (2) in order to create a passage (9) for the retention clip (3).

This extended spacer wing (4b) has also created sufficient passage (9) for the dental prosthesis (1) to rotate in one direction. Rotation in the opposite direction is inhibited by the close contact of the dental prosthesis (1) material against the indirect retainer surface (8) of the support section (2b) of the retention bar (2).

To facilitate the processing and aftercare of the dental prosthesis (1), a housing (11) is provided which fits the outer aspect of the spacer clip (4) and makes contact with the indirect retainer surface (8) of the support section (2b). The housing (11) guarantees a perfect seat for the retention clip (3) and at least one extremity has a slotted flange (12) with a slot diameter of the round section (2a). The slotted flange (12) guides the retention wings (5) of the retention clip (3) towards the centre of the round section (2a) when the dental prosthesis (1) is inserted by the patient.

In case the dental prosthesis (1) or the housing (11) for the dental prosthesis (1) is produced by CAD CAM technique, the spacer clip (4) is a virtual object and is first integrated with the retention bar (2) prior to the modeling of the dental prosthesis (1) or the housing (11).

The housing (11) can be produced with the lost wax technique, by milling, selective laser melting or machining, and is by preference of metal.

I claim:

1. A dental attachment system in combination with a dental prosthesis, the dental attachment system comprising
   a retention bar configured to be secured to crowns or dental implants in a mouth, the retention bar having a support section surmounted by a round section, the support section having an indirect retainer surface; and
   a generally flexible C-shaped retention clip having
      a pair of shoulders at an outer surface of the retention clip, the pair of shoulders snapping behind retention ledges in the dental prosthesis; and
      flexible retention wings clipping onto the round section of the retention bar; and
   the dental prosthesis comprising a housing;
   wherein the housing of the dental prosthesis contacts the indirect retainer surface of the support section; and
   wherein the housing has at least one extremity with a slotted flange.

2. The dental attachment system in combination with the dental prosthesis according to claim 1, wherein a passage is formed between a side surface of the support section of the retention bar and the housing; and wherein the side surface is opposite the indirect retainer surface.

3. The dental attachment system in combination with the dental prosthesis according to claim 2, wherein a center of the round section is closer to the side surface of the support section than the indirect retainer surface of the support section.

4. A dental attachment system in combination with a dental prosthesis, the dental attachment system comprising
   a retention bar configured to be secured to crowns or dental implants in a mouth, the retention bar having a support section surmounted by a round section, the support section having an indirect retainer surface; and
   a generally flexible C-shaped retention clip having
      a pair of shoulders at an outer surface of the retention clip, the pair of shoulders snapping behind retention ledges in the dental prosthesis; and
      flexible retention wings clipping onto the round section of the retention bar; and
   the dental prosthesis comprising a housing;
   wherein the housing of the dental prosthesis contacts the indirect retainer surface of the support section;
   wherein the housing has at least one extremity with a slotted flange; and
   wherein a diameter of the slotted flange is equal to a diameter of the round section.

* * * * *